United States Patent [19]

Rosemberg

[11] 4,196,123
[45] Apr. 1, 1980

[54] HYBRID CHORIONIC GONADOTROPIN PREPARATIONS AND METHODS FOR STIMULATING OVULATION USING SAME

[76] Inventor: Eugenia Rosemberg, 14 Ashland St., Worcester, Mass. 01609

[21] Appl. No.: 962,385

[22] Filed: Nov. 20, 1978

[51] Int. Cl.$^2$ .................... A61K 37/00; C07C 103/52; A61K 35/48
[52] U.S. Cl. ............................ 424/177; 260/112.5 R; 424/105
[58] Field of Search ............................ 424/105, 177; 260/112.5 R

[56] References Cited

PUBLICATIONS

Schlaff–Endocrinology, vol. 98, No. 2, (1976), pp. 527–533.
Merz et al.–Chem. Abst., vol. 79 (1973), p. 49985v.
Rao et al.–Chem. Abst., vol. 80 (1974), p. 10629c.

*Primary Examiner*—Delbert R. Phillips
*Attorney, Agent, or Firm*—David G. Conlin; George W. Neuner

[57] ABSTRACT

A hybrid hormone preparation comprising an admixture of α-chorionic gonadotropin subunits and β-chorionic gonadotropin subunits wherein the ratio of α subunits to β subunits is greater than 1:1, and methods for making and using such preparations, e.g. for stimulating ovulation in female mammals, is described.

37 Claims, 1 Drawing Figure

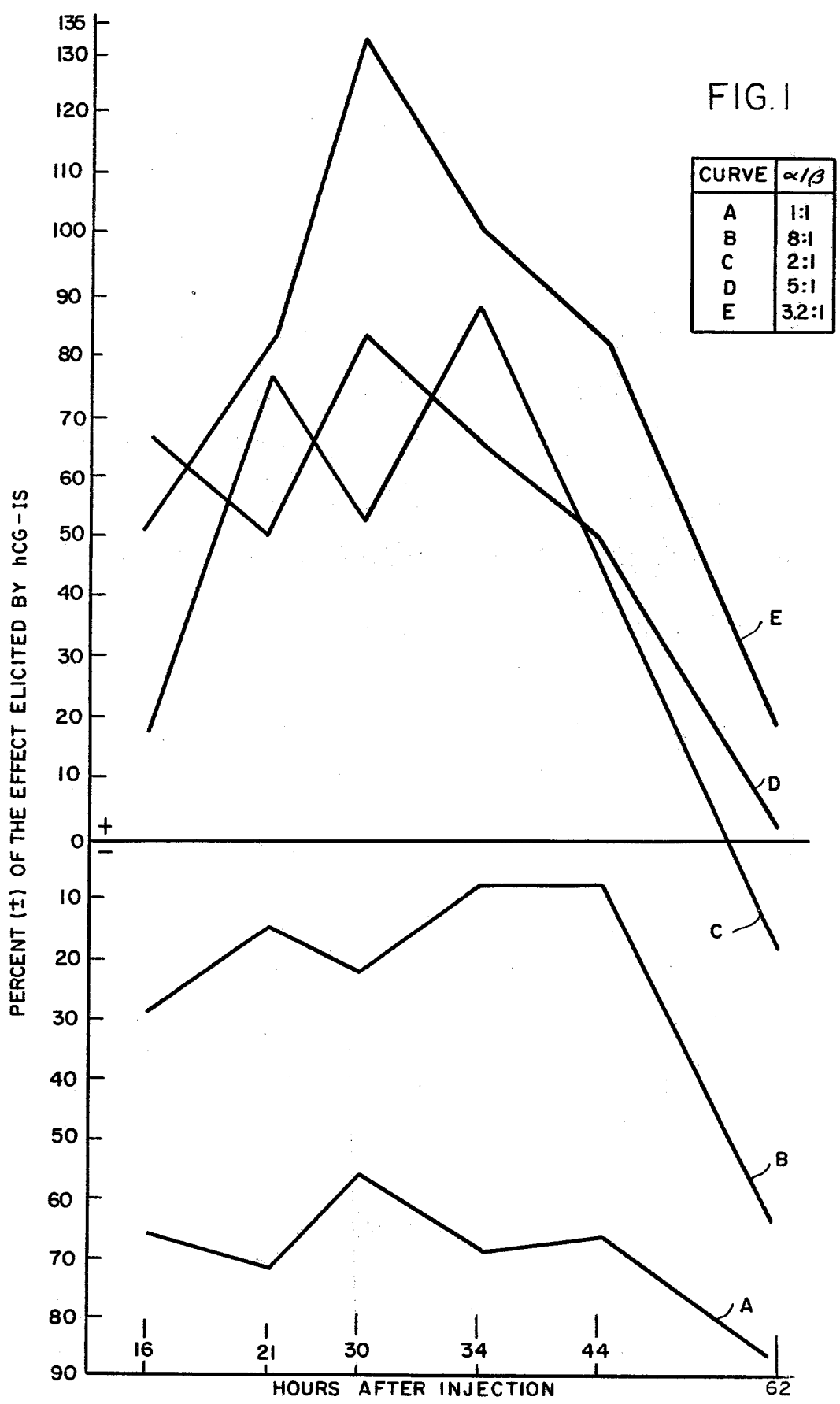

HYBRID CHORIONIC GONADOTROPIN PREPARATIONS AND METHODS FOR STIMULATING OVULATION USING SAME

FIELD OF THE INVENTION

This invention relates to gonadotropins and gonadotropin therapy, more particularly to the use of particular gonadotropin materials in stimulating ovulation in females, and particularly to human chorionic gonadotropin materials.

BACKGROUND OF THE INVENTION

Gonadotropic hormones, e.g. follicle-stimulating hormone (FSH) and luteinizing hormone (LH) are produced in the pituitary gland and control the function of both the ovaries and testes. After being secreted by the pituitary, under the influence of the hypothalamic gonadotropin releasing factor, FSH and LH circulate in the blood stream and thus are carried to and act on the ovaries or testes. Some of each of the hormones is removed from the blood by being metabolized and some is excreted in the urine. Chorionic gonadotropin (CG) is produced in the placenta and is excreted in the urine throughout pregnancy. Human chorionic gonadotropin (hCG), which is generally obtained by extraction from the urine of pregnant women, is commercially available, e.g., under the trade names Follutein and APL.

Gonadotropins have been found to be useful for many purposes in the treatment of both animals and humans. Chorionic gonadotropin (CG) has been found to be particularly useful in treatment of various conditions of the gonads (ovaries and testes) in humans and lower mammals. For instance, administration of CG to lower animal species will induce stimulation of immature gonads. Human chorionic gonadotropin (hCG) has generally been utilized in such work, since it is available commercially, and can be administered to other mammals.

HCG has been used for animal breeding purposes (e.g., the breeding of sheep, cattle, etc.). HCG has also been found useful in treating humans for: (1) induction of ovulation and pregnancy in the anovulatory infertile women; (2) treatment of female patients with disorders of the menstrual cycle; (3) treatment of threatened abortion; (4) treatment of female patients with luteal phase defects; (5) treatment of delayed adolescence; (6) treatment of selected causes of hypogonadotropic hypogonadism (males and females); (7) treatment of prepubertal cryptorchidism not due to anatomical obstruction; and (8) treatment of oligospermia.

Various hormone treatment schedules using gonadotropins have proved successful in treating infertility of female mammals to accomplish desired pregnancies. One type of treatment, particularly directed to treatment of infertility caused by inability to ovulate (anovulation), comprises daily administration of doses of luteinizing hormone (LH) and follicle stimulating hormone (FSH) for a prescribed period of time followed by the administration of one or more doses of human chorionic gonadotropin (hCG). LH and FSH are of pituitary or urinary origin (Human Menopausal Gonadotropin-Menotropins). If successful, the treatment will induce ovulation and thus make pregnancy possible.

Generally, a single dose of CG is used to induce ovulation after preparation of the ovaries for ovulation by treatment with the other hormones or estrogens. It has now been well established that women with many types of anovulation can be made to ovulate through the sequential administration of human gonadotropins, and such treatments have made parenthood possible for many women whose infertility had previously been considered incurable. See generally, Rosemberg, (ed.) *Gonadotropin Therapy in Female Infertility* (Excerpta Medica, Amsterdam 1973), which is incorporated herein by reference.

However, such treatments for anovulation, while successful, have been faced with major problems. A fairly well known problem which has occurred in some patients so treated is the occurrence of multiple pregnancies, in which the patient's ovary releases not just one, but a plurality of eggs or ovum, resulting in as many as eight, ten or even fifteen fetuses being produced (hereinafter referred to as "multiple gestation"). The reasons for multiple gestation have not been generally understood. Some have ascribed the cause as simply overdosage of the treatment hormones, resulting in overstimulation of the ovarian follicles which produce the ovum. That theory, and concern about other problems caused by hyperstimulation, have led to highly complex schemes for monitoring patient hormone levels during the period of treatment. However, while this approach has reduced the number of multiple gestations as compared to the early days of such infertility treatments, the multiple birth problem has simply had not been solved. Others have ascribed multiple gestations to the stimulation of follicles which contain more than one oocyte, thus considering the problem as an inherent problem of certain patient's ovaries, rather than a problem with the hormonal treatment.

Other problems which have been observed in gonadotropin therapy patients include what is referred to as ovarian hyperstimulation, which may evidence itself in enlargement of the ovaries, ascites (fluid in the peritoneal cavity) hypotension, hydrothorax (fluid in the pleural cavity), thrombophlebitis, and the development of ovarian cysts as well as other disorders. See generally, Rosemberg, supra, at 201–57. Again, close control of dosage and monitoring of hormone levels have reduced the occurrence of such problems, but have not solved them.

Thus, since the beginning of this type of treatment in the 1950's, ways have been continuously sought to find the proper method of treatment or material that would make the ovary respond appropriately to exogenous gonadotropin and accordingly present the desired condition for pregnancy without risk of multiple pregnancies or of undesirable and potentially serious side effects.

SUMMARY OF THE INVENTION

The invention herein comprises hybrid hormone preparations comprising a product of admixture of α-chorionic gonadotropin subunits and β-chorionic gonadotropin subunits, wherein the molar ratio of α subunits to β subunits is greater than 1.6:1. The use of such hormone preparations in the treatment of anovulation will alleviate the danger of overstimulation of the ovaries and thus reduce multiple pregnancies and other side effects, while still achieving effective inducement of ovulation.

In another aspect of my invention. there is provided a method for stimulating ovulation in female mammals that comprises administering a hybrid hormone preparation comprising a product of admixture of α-CG subunits and β-CG subunits wherein the ratio of α subunits to β subunits is greater than about 0.3:1.

BRIEF DESCRIPTION OF THE DRAWING

FIG. 1 is a graph illustrating the biological effect of certain embodiments of this invention over a period of time following administration.

DETAILED DESCRIPTION OF THE INVENTION

In accordance with the invention, a hybrid hormone preparation having a biological effect is obtained when CG subunits have α/β ratios greater than 1:1, e.g. advantageously about 1.6:1 to about 10:1, are admixed. Preferably, the α/β ratio is in the range of from about 2:1 to about 8:1 with the ratio of about 2.5:1 to about 5:1, e.g. about 3:1, being particularly preferred. The preparation is preferably administered intramuscularly to obtain the desired biological effect. When the preparation of this invention is used for the treatment of female mammals to stimulate ovulation, the danger of over-stimulation and multiple pregnancies is significantly reduced. Reduction of overstimulation will be effected by using any preparation in accord with the invention having an α/β ratio greater than about 0.3:1, preferably greater than 1:1.

Although not wishing to be bound by theory as to why the hybrid hormone preparation of this invention reduce the likelihood of overstimulation of the ovaries and, thus, the risk of multiple pregnancies, it is believed that this is due at least in part to a number of factors. One factor is believed to be the lower potentiation of hormone effect because the preparations of this invention generally contain more α subunits than β whereas commercial hCG contains more β subunits than α subunits. When the hormone preparations in this invention are administered intramuscularly, their metabolic degradation will result in an excess of free α-hCG over β-hCG subunits. Because the β-hCG subunit corresponds to the molecular structure in the complete hCG unit which is primarily responsible for the biological activity of hCG, it is believed that with less β-hCG reaching the ovary, the likelihood of potentiation of hCG effect which results in ovarian overstimulation will be diminished. Another beneficial factor results from the fact that the product of the present invention has a shorter half life in the blood stream than commercial hCG preparations, and thus the period of time over which excess stimulation can occur is reduced.

The invention will be described and exemplified with human chorionic gonadotropin (hCG) because hCG can be used in the treatment of other mammals. However, it will be appreciated by those skilled in the art that similar results can be obtained with other mammalian gonadotropins in non-human mammals, although such non-human gonadotropins cannot be used in humans, because the use of other mammalian gonadotropins in humans results in antibody-antigen reactions.

In the early 1970's, two groups of researchers were able to split hCG into its two subunits, α and β. See generally Morgan, et al. (Morgan), "Properties of Subunits of Human Chorionic Gonadotropins," Endocrinology, 94:1601 (June 1974), and references cited therein, which are hereby incorporated by reference.

The α and β subunits were reported as having little biological activity by themselves. The slight activity biologically exhibited by preparations of the subunits is due to their contamination with intact or whole hCG. Thus Morgan, supra, at 1601, reported that the biological activities of the subunits was less than 1% of the activity of native hCG. It was also reported that the subunits could be recombined to produce hCG which had biological specific activity in the rat ventral prostate weight (VPW) assay that was similar to the specific activity of native hCG.

Pierce, et al. (Pierce) "Biologically Active Hormones Prepared by Recombination of the Alpha Chain of Human Chorionic Gonadotropin and the Hormone-Specific Chain of Bovine Thyrotropin or of Bovine Luteinizing Hormone" J. Biol. Chem. 245:2321 (1971) reported by combining α and β subunits of different hormones with the results that the combined subunit hormone exhibited the biological effect attributed to the β subunit.

Thus, it was never remotely conceived that recombination of α and β subunits in ratios which differed from those found in native hCG would produce any useful physiological effect, or if useful, any substantially different physiological effect, much less than such materials could solve problems previously experienced in gonadotropin therapy.

For purposes of this invention "native hCG" is defined as any hCG that is obtained by extraction and is derived from a human source, whether further purified as in the case of hCG Canfield or not as in the case of commercial hCG.

In the present work, the α and β subunits of hCG were obtained from Dr. Robert Canfield, Department of Medicine College of Physicians and Surgeons, Columbia University, New York, New York. The α and β subunits were prepared by the method described in the Morgan, et al. reference, supra, "Properties of Subunits of Human Chorionic Gonadotropins," Endocrinology, 94, 5, p. 1601 (June 1974), which is hereby incorporated by reference. The α and β subunits are readily obtained from Dr. Canfield or from the National Institute of Health.

Preparation and Analysis of Materials

The α and β subunits of hCG were hybridized or recombined by admixing the subunits in various ratios. In all recombinations, the molecular weight of native hCG, and of α and β-hCG used in making calculations were:

| Preparation | Mean Molecular Weight |
| --- | --- |
| α-hCG subunit | 18,000 |
| β-hCG subunit | 29,000 |
| native hCG | 47,000 |

Stock solutions of preparations of the subunits were made with 1.6 to 8.1-fold molar excess of α-hCG to yield α/β ratios on molar basis of 1.6:1–2:1–3.2:1–5:1, and 8.1:1. A ratio of 1:1 was also made. The following table shows the quantities of subunits used for various preparations.

TABLE 1

| Molar Ratios α:β | A | | B | | C Total Wt (α + β) μg | D Vol Buffer λ (μl) | E Stock Solution Total Volume Buffer ml |
|---|---|---|---|---|---|---|---|
| | μgs → | | Moles | | | | |
| | α | β | α | β | | | |
| 1:1 | 180 | 290 | 0.01 | 0.01 | 470 | 470 | 47.0 |
| 1.6:1 | 200 | 200 | 0.0112 | 0.0069 | 400 | 400 | 40.0 |
| 2:1 | 180 | 145 | 0.01 | 0.005 | 325 | 325 | 32.5 |
| 3.2:1 | 200 | 100 | 0.0112 | 0.00345 | 300 | 300 | 30.0 |
| 5:1 | 450 | 145 | 0.0252 | 0.005 | 595 | 595 | 29.75 |
| 8.1:1 | 500 | 100 | 0.0278 | 0.00345 | 600 | 600 | 30.0 |

With reference to Table 1 above, the amounts (βgs) of each subunit used for recombination or hybridization are shown in column A; the corresponding moles are shown in column B. For each recombination, the combined weight (α+β, column C) was dissolved in 0.01 M phosphate buffer, pH 7.0 (volumes of buffer shown in column D) mixed by Vortex, and incubated for 16 hrs. at 37° C. After incubation, each sample was diluted to the volume of buffer shown in column E to prepare stock solutions with concentrations of 10 or 20 μg of the combined weight of α+β-hCG per ml of buffer. After recombination, no attempts were made to remove "free" subunits by gel filtration.

Sub-stock solutions containing 1, 0.1 and 0.01 μg/ml in 0.01 M phosphate buffer, ph 7, were prepared and utilized immediately in radioimmunoassays (RIA's). The sub-stock solutions were stored frozen until further use in RIA's and Bioassays. Controls consisting of single subunits and native hCG preparation (i.e.: hCG Canfield) were similarly treated.

The RIA's were performed following the double antibody procedure described by Odell et al, *J. Clin. Invest.*, 46, p. 248 (1967). The RIA's used were: (1) a homologous hCG system, utilizing a purified preparation of hCG as label, and an anti hCG serum used at a final dilution of 1:200,000; (2) an α-hCG subunit system utilizing α-hCG as label, and an anti α-hCG serum used at a final dilution of 1:400,000, and (3) β-hCG subunit system utilizing highly purified hCG as label and an anti-β-hCG serum at a final dilution of 1:180,000. $^{125}$I was used for iodination of antigens following the procedure described by Odell, et al.

Various dose levels of each hybrid preparation as well as native hCG, purified hCG Canfield,[1] hCG-IS[2] and α and β-hCG were tested in the homologous hCG, hCGα and hCGβ RIA systems, respectively. All RIA's were initially incubated for 24 hrs. at 24° C. Second antibody (goat antirabbit gamma globulin) was then added and the incubation continued for 18 hrs. at 24° C. Bound and free antigens were separated by centrifugation. Results of the immunoassay were plotted as the logit transformation of the response variate, further normalized to maximum counts bound $B_o$, versus log dose of antigen. All RIA assays were calculated using appropriate computer programs and the results are tabulated below.

[1] hCG Canfield is a preparation of native hCG purified in accord with the procedures described in Peptide Hormones, edited by Berson, et al. Chapter 1, "Human Chorionic Gonadotropin (hCG)" by Canfield, et al., pp. 727-742, which is hereby incorporated by reference.
[2] hCG-IS is a preparation of hCG prepared by the World Health Organization (W.H.O.) for use as an International standard by extraction of hCG from the urine of pregnant women (W.H.O. Technical Report Series, No. 413, 1969). This International standard is distributed on behalf of W.H.O. by the Division of Biological Standards, National Institute for Medical Research, Mill Hill, London N.W. 7, England.

TABLE 2

DOSE LEVELS USED IN RIA'S

| PREPARATIONS | hCG HOMOLOGOUS SYSTEM DOSE - ng | α-hCG SYSTEM DOSE - ng | β-hCG SYSTEM DOSE - ng |
|---|---|---|---|
| hCG Canfield | 1-2-3-5-10 | 0.5-1-2-3-5-10 | 0.5-1-2-3-5-10 |
| hCG IS | 2.6-5.2-6.5-13-26 | 0.65-1.3-2.6-5.2-6.5-13 | 0.65-1.3-2.6-5.2-13-26 |
| α-hCG | 10-20-50-100-200 | 0.1-0.2-0.5-1-2 | 2-5-10-20-50 |
| β-hCG | 1-2-5-10-20-50-100 | 20-50-100-200-400 | 0.5-0.1-0.2-0.3-0.5-1 |
| Recombinations | | | |
| (α−β ratios) | | | |
| A (1:1) | 0.5-1-2-5-10-20+ | 0.2-0.3-0.5-1-2-5-10+ | 0.2-0.3-0.5-1-2-5-10-20-50-100+ |
| B (1.6:1) | 0.5-1-2-5-10-20 | 0.2-0.3-0.5-1-2-5-10 | 0.2-0.3-0.5-1-2-5-10-20-50-100 |
| C (2.0:1) | 0.2-0.5-1-2-5-10-20 | 0.2-0.3-0.5-1-2-5-10 | 0.2-0.3-0.5-1-2-5-10-20-50-100 |
| 0.2-0.3-0.5-1-2-5-10 | 0.2-0.3-0.5-1-2-5-10-20-50-100 | | |
| E (5.0:1) | 0.5-1-2-5-10-20 | 0.2-0.3-0.5-1-2-5-10 | 0.2-0.3-0.5-1-2-5-10-20-50-100 |
| F (8.1:1) | 0.5-1-2-5-10-20 | 0.2-0.3-0.5-1-2-5-10 | 0.2-0.3-0.5-1-2-5-10-20-50-100 |

† Dose levels based on the combined weight of α + β-hCG used for each hybridization.

Table 3 presents the potency of the α and β-hCG subunits, and of the various α and β-hCG recombinations in terms of (1)—the purified hCG preparation (Canfield's), and (2)—of the International standard of hCG (hCG-IS). It should be noted that the slope of β-hCG was non-parallel to that of the other preparations, however, the slopes of all other preparations tested were not significantly different from each other. Hybridizations A to C (1:1 to 2:1) were twice as potent as hCG Canfield: D (3.2:1) was 1.6 times, and E (5:1) was 1.4 times more potent than hCG Canfield: F (8.1:1) was equipotent to hCG Canfield.

TABLE 3

RIA OF HCG, α AND β-hCG, AND OF hCG SUBUNIT HYBRIDS
HOMOLOGOUS RIA hCG SYSTEM

| PREPARATIONS | RELATIVE POTENCY+ (CONFIDENCE LIMITS) | | | RELATIVE POTENCY+ (CONFIDENCE LIMITS) | | | SLOPE | MED++ |
|---|---|---|---|---|---|---|---|---|
| hCG Canfield | 1 | | | 3.3 | (2.8–3.7) | | −1.2 | 2.5 ng |
| hCG-IS | 0.32 | (0.27–0.37) | ng/ng | 1 | | | −1.2 | 7.9 ng |
| α-hCG | 0.16 | (0.12–0.21) | ng/ng | 0.51 | (0.41–0.66) | ng/ng | −.12 | 16.2 ng |
| β-hCG | 0.08 | (0.04–0.13) | ng/ng | 0.35 | (0.21–0.55) | ng/ng | −0.3** | 31.7 ng |
| Recombinations | | | | | | | | |
| (α−β ratios) | | | ng/ng* | | | | | |
| A (1:1) | 2.2 | (1.6–3.2) | | 7.1 | (5.4–9.6) | | −1.2 | 1.1 ng |
| B (1.6:1) | 2.2 | (1.5–2.4) | | 6.9 | (5.2–9.3) | | −1.2 | 1.2 ng |
| C (2.0:1) | 2.0 | (1.3–3.1) | | 6.6 | (4.8–9.4) | | −1.1 | 1.2 ng |
| D (3.2:1) | 1.6 | (1.1–2.2) | | 5.0 | (3.8–6.8) | | −1.1 | 1.7 ng |
| E (5.0:1) | 1.4 | (1.1–1.7) | | 4.1 | (3.4–5.1) | | −1.2 | 1.8 ng |
| F (8.1:1) | 1.1 | (0.9–1.3) | | 3.3 | (2.7–4.0) | | −1.2 | 2.4 ng |

+ Mean of 3 assays.
++ Median Effective Dose (50% Binding).
*Relative Potency based on the combined total of α + β-hCG used for each hybridization.
**non-parallel.

Table 4 presents the α and β content of the two hCG preparations of the α and β-hCG subunits, and of the various hybrid hCG preparations studied in the α and β-hCG RIA systems.

TABLE 4
RIA OF hCG, α AND β-hCG, AND OF hCG SUBUNIT HYBRIDS

| PREPARATIONS | RIA α-hCG SYSTEM | | | | RIA β-hCG SYSTEM | | | |
|---|---|---|---|---|---|---|---|---|
| | RELATIVE POTENCY (CONFIDENCE LIMITS) | | SLOPE | MED+ | RELATIVE POTENCY (CONFIDENCE LIMITS) | | SLOPE | MED+ |
| α-hCG | 1 | | −0.9 | 0.4 ng | 0.03 | (0.02–0.04) ng/ng | −1.0 | 7.0 ng |
| hCG Canfield | 0.07 | (0.06–0.09) ng/ng | −0.8 | 5.8 ng | 0.12 | (0.10–0.15) ng/ng | −0.9 | 1.8 ng |
| hCG IS | 0.03 | (0.02–0.04) ng/ng | −0.8 | 12.6 ng | 0.10 | (0.08–0.12) ng/ng | −0.8 | 2.3 ng |
| β-hCG | 0.0009 | (0.0006–0.001) | −1.3 | 404.0 ng | | 1 | −1.0 | 0.2 ng |
| Recombinations (α/β ratios) | | | | | | | | |
| A (1:1) | 0.37 | (0.32–0.44) ng/ng* | −1.1 | 1.1 ng | 0.45 | (0.36–0.54) | −1.0 | 0.5 ng |
| B (1.6:1) | 0.43 | (0.37–0.41) | −1.0 | 0.9 ng | 0.31 | (0.27–0.36) | −1.0 | 0.7 ng |
| C (2.0:1) | 0.48 | (0.41–0.55) | −1.0 | 0.8 ng | 0.33 | (0.27–0.41) | −0.9 | 0.7 ng |
| D (3.2:1) | 0.56 | (0.50–0.67) | −0.9 | 0.7 ng | 0.17 | (0.14–0.21) | −0.8 | 1.3 ng |
| E (5.0:1) | 0.65 | (0.53–0.80) | −1.0 | 0.6 ng | 0.13 | (0.10–0.15) | −0.8 | 1.8 ng |
| F (8.1:1) | 0.66 | (0.57–0.77) | −1.0 | 0.6 ng | 0.11 | (0.09–0.13) | −0.8 | 2.2 ng |

+Median Effective Dose (50% binding).
*Relative Potency based on the combined weight of α + β-hCG used for each hybridization.

Table 5 is a summary of the RIA's and shows the specific activity (Relative Potency) of the preparations in the homologous hCG system expressed in terms of hCG Canfield and hCG-IS (data from Table 3), and the percent columns 1 and 2 (data from Table 4) of α and β-hCG subunits contained in each hybrid measured in the α and β-hCG systems, as well as their respective α/β and β/α ratios (columns 3 and 4). It should be noted that the α/β ratios increase as the α content of the hybrids increases.

TABLE 6B

| α/β Ratios | For 5,000 IU hCG-IS Ampoules | | | |
|---|---|---|---|---|
| | α-hCG | | β-hCG | |
| | moles | (μg) | moles | (μg) |
| 1:1 | 0.027 | (450) | 0.027 | (772) |
| 2:1 | 0.027 | (450) | 0.0135 | (386) |
| 3:1 | 0.027 | (450) | 0.009 | (257) |
| 5:1 | 0.054 | (900) | 0.011 | (314) |

TABLE 5

RIA of hCG, α and β-hCG, AND OF hCG SUBUNIT HYBRIDS

| PREPARATIONS | RIA HOMOLOGOUS hCG SYSTEM RELATIVE POTENCY | RIA α AND β hCG-SUBUNIT SYSTEMS | | RATIOS [FROM COLUMNS (1) (2)] | |
|---|---|---|---|---|---|
| | | % α+ (1) | % β+ (2) | α/β (3) | β/α (4) |
| hCG Canfield | 1 | 3.3 | 7.4 | 12.0 | 0.61 | 1.6 |
| hCG IS | 0.32 | 1 | 3.0 | 10.0 | 0.3 | 3.3 |
| α-hCG | 0.16 | 0.51 | 100.0 | 3.0 | | |
| β-hCG | 0.08 | 0.35 | 0.09 | 100.0 | | |
| Recombinations | | | | | | |
| (α/β ratios) | | | | | | |
| A (1:1) | 2.2 | 7.1 | 37.0 | 45.0 | 0.82 | 1.2 |
| B (1.6:1) | 2.2 | 6.9 | 43.0 | 31.0 | 1.4 | 0.72 |
| C (2.0:1) | 2.0 | 6.6 | 48.0 | 33.0 | 1.5 | 0.69 |
| D (3.2:1) | 1.6 | 5.0 | 58.0 | 17.0 | 3.4 | 0.29 |
| E (5.0:1) | 1.4 | 4.1 | 65.0 | 13.0 | 5.0 | 0.20 |
| F (8.1:1) | 1.1 | 3.3 | 66.0 | 11.0 | 6.0 | 0.17 |

* % Contamination with α or β-hCG calculated from Table 3.

Commercial preparations of hCG are packaged for use in ampoules containing the equivalent to 5,000 or 10,000 IU's of hCG-IS activity. I have found by RIA that the content of α and β-hCG in commercial hCG preparations are: 29 ng of α-hCG, and 90 ng of β-hCG per 1 IU. Therefore, 10,000 IU's of commercial hCG contains 290 μg (or 0.0162 moles) of α-hCG and 900 μg (or 0.03 moles) of β-hCG; 5,000 IU's of commercial hCG contain half these amounts, i.e.,: 145 g (0.0081 moles) of α-hCG, and 450 μg (0.015 moles) of β-hCG.

The international unit (IU) is defined as the specified biological activity contained in a defined weight of a current international standard. The standard is the material as it exists in the ampoules; the "material" thus includes the active ingredients together with all the other constituents such as moisture and in some instances carrier and buffer salts.

Hormone preparations in accord with my invention are also advantageously packaged for use in ampoules containing the equivalent to 5,000 to 10,000 IU's of hCG-IS activity. Based on the data with respect to activity of the hybrid preparations of my invention, examples of ampoules of hybrid preparations in accord with the present invention would be prepared containing α and β subunits as follows (See Table 6A and 6B):

TABLE 6A

| α/β Ratios | For 10,000 IU hCG-IS Ampoules | | | |
|---|---|---|---|---|
| | α-hCG | | β-hCG | |
| | moles | (μg) | moles | (μg) |
| 1:1 | 0.054 | (900) | 0.054 | (1,543) |
| 2:1 | 0.054 | (900) | 0.027 | (771) |
| 3:1 | 0.054 | (900) | 0.018 | (514) |
| 5:1 | 0.108 | (1,800) | 0.022 | (628) |

Preferably, the α and β hCG subunits should contain no more than 5% contamination with native hCG.

Pharmacological preparations in accord with my invention may also be produced as, for instance, tablets, pills or capsules for oral administration; suppositories, for example, for intravaginal administration; ampoules of material as noted above for injection, for example, intramuscularly or intravenously; etc. Pharmaceutically acceptable, organic or inorganic, solid or liquid carriers may be used, suitably for oral or parenteral administration, in manufacturing the preparation. Gelatine, lactose, starch, magnesium stearate, micronized silica gel, cocoa butter, talc, vegetabilic and animalic fats and oils, vegetabilic rubber and polyalkylene glycol and other known carriers for pharmaceuticals are all suitable for manufacturing preparations of said compounds. Preparations for parenteral use include an ampoule of a sterile solution or suspension with water or other pharmaceutically acceptable liquid as the carrier therefor, or an ampoule of sterile powder for dilution with a pharmaceutically acceptable liquid.

Hormone preparations in accord with my invention are useful for many purposes in the treatment of both animals and humans. For instance, administration of hormone preparations of this invention to lower animal species will induce stimulation of immature gonads (ovaries and testes). Thus, these preparations are a very important tool in the in vivo as well as the in vitro (radioassay) study of the processes involved in reproduction and in the study of the immunological and biological characteristics of the hCG molecule.

The hormone preparations of this invention can also be utilized for animal breeding purposes (e.g., the breeding of sheep, cattle, etc.). Preparations having α/β ratios greater than 0.3:1 are useful although ratios greater than 1:1 and less than about 5:1 are particularly useful for this purpose with the preparation having an α/β ratio of about 3:1 being most preferred. The hormone preparations of this invention are also useful in treating infertility in monkeys used for research purposes in the Primate Centers in the United States and elsewhere. α/β ratios preferred for this purpose are the same as above.

The hormone preparations of my invention are also useful in treating humans, for example, for:

(1) Induction of ovulation and pregnancy in the anovulatory infertile women in whom the cause of anovulation is secondary, and not due to primary ovarian failure, and who has been appropriately treated with human menotropins (Human Menopausal Gonadotropin);
(2) Treatment of female patients with disorders of the menstrual cycle;
(3) Treatment of female patients with luteal phase defects;
(4) Treatment of threatened abortion;
(5) Treatment of delayed adolescence;
(6) Treatment of selected cases of hypogonadotropicHypogonadism (males and females);
(7) Treatment of prepubertal cryptorchidism not due to anatomical obstruction; and
(8) Treatment of oligospermia;

The hormone preparations of my invention are usually administered by the intramuscular route.

For application 1, induction of ovulation and pregnancy, hormone preparations with α/β ratios greater than 1:1 and less than about 5:1 are preferred. The most preferred ratio will be about 3:1. The hybrid should be administered at a dose equivalent to 5,000 or 10,000 IU hCG-IS, one day after the administration of the last dose of menotropins. Menotropins should be administered at daily dosages of 75 to 150 IU of FSH activity for 6 days. Treatment should be started 7 days prior to the administration of the hybrid.

For application 2, the preparation should preferably be administered at a daily dose equivalent to 1,000 IU hCG-IS from day 3 to 9 of the menstrual cycle.

For application 3, the preparation should preferably be administered at a daily dose equivalent to 1,000 IU hCG-IS from day 16 to 24 of the menstrual cycle.

For application 4, the preparation should preferably be administered at a daily dose equivalent to 2,000 IU hCG-IS for the length of time necessary to control the condition.

For application 5, the preparation should preferably be administered at a daily dose equivalent to 1,000 IU hCG-IS activity for a period of 15 to 20 days or longer depending on clinical response.

For application 6, the preparation should preferably be administered at a dose equivalent to 2,000 to 3,000 IU hCG-IS every other day for a period of two to three months.

For application 7, the preparation should preferably be administered at a dose equivalent to 1,000 IU hCG IS three times weekly for 3 weeks. If this course is not effective, another should begin one month later, administering the hybrid at a dose equivalent to 2,000 IU hCG-IS three times weekly for a period of three weeks.

For application 8, the preparation should preferably be administered at a dose equivalent to 2,000 to 3,000 IU hCG-IS three times weekly for periods of 3 to 6 months or longer according to clinical response.

The following examples are provided to further illustrate the invention.

BIOASSAY-MOUSE UTERINE WEIGHT ASSAY (MUWtA)

The mouse uterine weight assay was used to measure the biologic activity of hCG-Canfield, hCG-IS and of the various recombinations of α and β-hCG subunits. The bioassay employs as the end-point the uterine weight increase in 21 day-old intact Swiss albino rats. The bioassay method was carried out as previously described by Rosemberg et al, *J. Clin. Endrocrinol. Metab.*, 22, p. 953, (1962), which is hereby incorporated by reference.

The total dose for injection of each material was prepared from stock solutions (for preparation of stock solutions refer to Table 1 and discussion above). The solution was such that the total fluid injected into each mouse was 2.5 ml. The total dose was divided into 5 single subcutaneous injections of 0.5 ml each, given during the course of 3 days. Autopsies were carried out about 72 hours after the first injection. The uteri were cut out at the insertion of the oviducts and immediately distal to the cervix uteri; they were dissected, pressed between filter papers and weighed at once in a Roller-Smith torsion balance. Potency estimates were calculated by standard statistical methods for valid parallel line graded dose assays.

hCG-IS was tested in the MUWtA in order to show the effect of varying dose levels of hCG in this bioassay system.

| hCG - IS Dose in IU's | (ng) | Uterine Weight (mg)[+] Mean | (± SE) |
|---|---|---|---|
| Controls | (saline) | 12.2 | (0.4) |
| 0.06 | (78) | 15.7 | (1.4) |
| 0.12 | (156) | 31.2 | (2.3) |
| 0.25 | (325) | 49.0 | (7.8) |
| 0.5 | (650) | 58.7 | (7.0) |

[+]25 animals per dose level

A graded response was obtained with increasing doses of the preparation.

EXAMPLES 1–7

Purified hCG Canfield, hCG-IS and the various α/β-hCG hybrid preparations were tested at two dose levels i.e.: hCG Canfield: 1.2 and 2.5 ng; hCG-IS: 156 and 325 ng. The hybrid preparations were tested at 1.2 and 2.5 ng (doses were based on the combined weight of α+β-hCG used for hybridization). The results of the biological testing are presented in Tables 7A and 7B.

Table 7A

| | BIOASSAY OF hCG, AND OF α/β hCG HYBRID PREPARATIONS IN PHOSPHATE BUFFER SOLUTION (PBS) | | |
|---|---|---|---|
| EX. NO. | PREPARATIONS[+] | UTERINE WT* RELATIVE POTENCY (CONFIDENCE LIMITS) | RATIO: UTERINE WT/BODY WT** RELATIVE POTENCY (CONFIDENCE LIMITS) |
| 1 | hCG Canfield | 1 | 1 |

Table 7A-continued

BIOASSAY OF hCG, AND OF α/β hCG HYBRID PREPARATIONS
IN PHOSPHATE BUFFER SOLUTION (PBS)

| EX. NO. | PREPARATIONS+ | UTERINE WT* RELATIVE POTENCY (CONFIDENCE LIMITS) | RATIO: UTERINE WT/BODY WT** RELATIVE POTENCY (CONFIDENCE LIMITS) |
|---|---|---|---|
| 2 | hCG-IS | 0.16 (0.11–0.39) μg/IU | 0.18 (0.13–0.34) μg/IU |
|  | Recombinations (α/β ratios) |  |  |
| 3 | (1:1) | 0.90 (0.73–1.10)# | 0.93 (0.72–1.19)# |
| 4 | (2.0:1) | 1.17 (0.87–1.74) | 1.24 (0.91–1.92) |
| 5 | (3.2:1) | 0.79 (0.60–1.0) | 0.85 (0.63–1.11) |
| 6 | (5.0:1) | 0.62 (0.44–0.79) | 0.60 (0.37–0.81) |
| 7 | (8.1:1) | 0.45 (0.30–0.58) | 0.42 (0.22–0.59) |

+ Final solutions for injection in 0.01 M PBS buffer, pH 7.
*, **End point of assay.
Relative Potency based on the combined weight of α + β-hCG used for each hybridization. (μg/μg).

TABLE 7B

BIOASSAY OF hCG, AND OF α/β hCG HYBRID PREPARATIONS
IN 0.9% SALINE

| EX. NO. | PREPARATIONS+ | UTERINE WT* RELATIVE POTENCY (CONFIDENCE LIMITS) | RATIO: UTERINE WT/BODY WT** RELATIVE POTENCY (CONFIDENCE LIMITS) |
|---|---|---|---|
| 1 | hCG Canfield | 1 | 1 |
| 2 | hCG IS | 0.14 (0.10–0.24) μg/IU | 0.14 (0.10–0.25) μg/IU |
|  | Recombinations (α/β ratios) |  |  |
| 3 | (1:1) | 0.89 (0.63–1.20)# | 0.90 (0.67–1.17)# |
| 4 | (2.0:1) | 1.0 (0.78–1.29) | 0.98 (0.76–1.24) |
| 5 | (3.2:1) | 0.99 (0.77–1.26) | 1.02 (0.81–1.28) |
| 6 | (5.0:1) | 0.73 (0.55–0.90) | 0.73 (0.56–0.89) |
| 7 | (8.0:1) | 0.49 (0.27–0.68) | 0.47 (0.27–0.64) |

+ Final solutions for injection in 0.9% saline.
*; **end point of assay;
Relative Potency based on the combined weight of α + β-hCG used for each hybridization. (μg/μg)

Tables 7A and 7B show the specific activity (Relative Potency) of hCG-IS, and of the various hybrid preparations in terms of purified hCG Canfield. Biologic activity was restored when complementary subunits α and β of hCG were hybridized. The greatest biologic activity was attained with hybrids containing α/β ratios of 1:1 and 2:1, and 3.2:1. These hybrids were equipotent to hCG Canfield. Hybrids containing α/β ratios of 5:1 showed about 60% of the biologic activity present in hCG Canfield. Hybrids containing α/β ratios of 8:1 showed about 40 (+)% of the biologic activity present in hCG Canfield. There were no significant differences in the specific activities when the vehicle used for administration of the preparations was PBS (phosphate buffer solution) buffer (Table 7A) or 0.9% saline (Table 7B).

It should be noted that hCG Canfield (purified native hCG) is about 6 times more potent than hCG-IS which has a potency equivalent to commercial hCG. Therefore, the hybrid preparations of my invention can be at least 6 (+) times more potent than commercial hCG and hCG-IS.

Table 8 provides a tabulation of the characteristics of the assay, i.e. the value of individual slopes and of the index of precision of the assay (λ).

TABLE 8

BIOASSAY CHARACTERISTICS

| EX. NO. | PREPARATIONS | UTERINE WT+ SLOPE (±SE) | λ | UTERINE WT BODY WT+ SLOPE (±SE) | λ | UTERINE WT++ SLOPE (±SE) | λ | UTERINE WT++ BODY WT SLOPE (±SE) | λ |
|---|---|---|---|---|---|---|---|---|---|
| 1 | hCG Canfield | 136 (21) | 0.05 | 7.5 (1.6) | 0.11 | 145 (32) | 0.11 | 9.5 (1.9) | 0.09 |
| 2 | hCG-IS | 74 (47) | 0.31 | 6.4 (2.5) | 0.21 | 66 (34) | 0.21 | 3.2 (2.1) | 0.20 |
|  | Recombinations (α/ ratios) |  |  |  |  |  |  |  |  |
| 3 | (1:1) | 121 (24) | 0.07 | 8.2 (1.7) | 0.10 | 142 (43) | 0.16 | 9.5 (2.6) | 0.12 |
| 4 | (2.0:1) | 144 (49) | 0.17 | 9.9 (3.0) | 0.18 | 119 (23) | 0.11 | 6.6 (1.5) | 0.10 |
| 5 | (3.2:1) | 73 (23) | 0.10 | 5.7 (1.4) | 0.12 | 131 (26) | 0.10 | 8.5 (1.6) | 0.09 |
| 6 | (5.0:1) | 49 (17) | 0.01 | 3.1 (1.1) | 0.16 | 110 (14) | 0.08 | 6.9 (1.0) | 0.07 |
| 7 | (8.0:1) | 30 (10) | 0.09 | 1.9 (0.6) | 0.15 | 46 (16) | 0.16 | 2.7 (1.0) | 0.13 |

+ Injecting vehicle: PBS buffer;
++ Injecting vehicle: 0.9% saline

EXAMPLE 8

The effect of freezing on the immunological reactivity of native hCG, α-hCG and hybrid preparations was determined by assaying in the homologous hCG RIA system immediately after preparation and then freezing the solutions. The solutions were then stored frozen for a period of three or four weeks and defrosted three time each during the period. RIA's were seen again at the end of the respective periods. The results are tabulated below in Table 9.

TABLE 9
EFFECT OF FREEZING
RIA - HOMOLOGOUS hCG SYSTEM

| | A | B |
|---|---|---|
| PREPARATION | RELATIVE POTENCY+ (CONFIDENCE LIMITS) | RELATIVE POTENCY++ (CONFIDENCE LIMITS) |
| hCG Canfield | | 0.86 (0.78–0.95) |
| hCG-IS | | 1.08 (0.93–1.25) |
| α-hCG | 0.90 (0.60–1.33) | |
| Recombinations (α/β ratios) | | |
| (1:1) | 1.0 (0.71–1.42) | 0.99 (0.56–1.74) |
| (1.6:1) | 0.98 (0.65–1.49) | 1.07 (0.64–1.82) |
| (2.0:1) | | 1.02 (0.63–1.66) |
| (3.2:1) | | 1.05 (0.71–1.54) |
| (5.0:1) | 1.0 (0.78–1.28) | |
| (8.1:1) | 1.15 (0.94–1.41) | |

A, B: Stocks of hCG's, α-hCG and α/β hybrids were frozen for three weeks (A) and four weeks (B) prior to RIA. The preparations were defrosted three times each prior to RIA, respectively.
+; ++ Relative Potency in terms of each preparation.

The results tabulated in Table 9 illustrate that the preparations retained substantially full immunoreactivity.

The dosages used were calculated to exceed the minimal dose (MD) causing an increase in uterine weight singnificantly different from controls.

For hCG Canfield, the amount given was 7 times higher than its MD dose. The dosages used for all other preparations i.e.: hCG-IS and hCG hybrids were calculated to equal or exceed that of hCG Canfield (biologic potency). The doses used are tabulated in Table 10 below.

TABLE 10

| Ex. NO | PREPARATIONS | DOSE (μg) | Biological Activity in terms of hCG Canfield (μg equivalent of hCG Canfield) |
|---|---|---|---|
| 9 | hCG Canfield | 0.08 | 1 (or 0.08 μg) |
| 10 | hCG-IS | 0.975 (0.75 IU) | 1.3 (or 0.107 μg) |
| | Recombinations (α1β ratios) | | |
| 11 | (1:1) | 0.12 | 3 (or 0.32 μg) |
| 12 | (2:1) | 0.08 | 1 (or 0.08 μg) |
| 13 | (3.2:1) | 0.10 | 0.8 (or 0.06 μg) |
| 14 | (5:1) | 0.12 | 0.8 (or 0.06 μg) |
| 15 | (8:1) | 0.24 | 1.7 (or 0.14 μg) |

Table 11 shows the end organ response (uterine weight/body weight ratio) at each time interval after the administration of a single dose of each preparation. Except for hCG Canfield, all other preparations elicited a significant increase in uterine weight 16 hours after injection. All preparations elicited a sustained increase in uterine weight from 24 to 62 hours after injection.

Analysis of the data was carried out by calculating each response at each time interval as a ± percent of the response recorded for hCG-IS at the same time interval. In these calculations, the doses of the various hCG hybrids, and of hCG Canfield, were equalized to that of 1 μg of hCG-IS.

TABLE 11
BIOLOGIC EFFECT OF A SINGLE DOSE OF NATIVE hCG AND OF hCG HYBRIDS

| | | HOURS AFTER INJECTION | | | | | | | |
|---|---|---|---|---|---|---|---|---|---|
| | | 4 | 8 | 16 | 24 | 30 | 38 | 44 | 62 |
| | | Ut Wt* | Ut Wt | Ut Wt | UT Wt | Ut Wt | Ut Wt | Ut Wt | Ut Wt |
| EX. NO. | PREPARATIONS | Body Wt | Body Wt | Body Wt | Body Wt | Body Wt | Body Wt | Body Wt | Body Wt |
| | Controls | 0.74 | 0.77 | 0.94 | 0.81 | 0.80 | 0.87 | 0.88 | 0.90 |
| 9 | hCG Canfield | 0.92 | 0.87 | 1.02 | 2.42 | 2.36 | 1.97 | 2.51 | 1.98 |
| 10 | hCG IS | 0.76 | 0.86 | 1.46 | 1.71 | 1.89 | 1.58 | 2.45 | 3.18 |
| | Recombinations (α/β ratios) | | | | | | | | |
| 11 | (1:1) | 1.03 | 1.01 | 1.36 | 1.52 | 2.44 | 2.01 | 1.44 | 1.34 |
| 12 | (2:1) | 0.82 | 1.08 | 1.38 | 2.44 | 2.20 | 2.07 | 2.72 | 2.10 |
| 13 | (3.2:1) | 0.98 | 0.90 | 1.21 | 1.76 | 2.48 | 1.79 | 2.33 | 1.96 |
| 14 | (5:1) | 0.79 | 0.87 | 1.34 | 1.47 | 1.97 | 1.81 | 1.99 | 1.79 |
| 15 | (8:1) | 0.71 | 0.96 | 1.41 | 1.88 | 1.96 | 1.95 | 2.96 | 2.41 |

*Mean of 4 observations (mg).

EXAMPLES 9–15

Time studies were conducted using various hybrid preparations to determine the duration of the hormone effect. The uterine weight increase in 21 day old immature female mice was used as the response metameter. Animals were divided in 10 groups consisting of 4 animals per group. A single injection of native hCG and of α-β hCG hybrids were administered at 0 time. Autopsies were performed as previously described 4, 8, 16, 24, 30, 38, 44 and 62 hours later. Suitable controls were also examined at each time interval.

FIG. 1 is a graph illustrating the effect of the administration of the hybrid preparations as a percent of the effect elicited by hCG-IS shown in Examples 8–14. FIG. 1 shows that from 16 to 44 hours after injection, all hCG hybrids except Curve A (α/β, 1:1) and Curve B (α/β, 8:1), elicited a response higher than that of hCG-IS. hCG Canfield (not shown) showed a higher response from 24 to 44 hours after injection. At 44 hours, the effect of hybrids Curve E (α/β, 3.2:1) and Curve B (α/β, 8:1) and of hCG Canfield was increased. At 62 hours, all preparations showed a sharp decrease in activity compared to that of hCG-IS.

EXAMPLE 16

A pharmacological preparation of the hybrid hormone of this invention is prepared for injection in the following manner. First, α-hCG subunits and β-hCG subunits are combined in the desired molar ratio, for example, 3 m moles α-hCG/1 m mole β-hCG, and dissolved in 0.01 M phosphate buffer, pH 7.0. At least one ml of buffer should be used for each mg of combined weight of the subunits. The mixture is mixed by Vortex and incubated at 37° C. for 16 hours after which the mixture is diluted by 100 fold and the recombined material is lyophilized. Lactose in an amount of from 0.1 to 1.0% of the dilute solution can be added prior to lyophilization to aid in redissolving. The lyophilized material is then weighed into sterile ampoules in accord with Tables 6A and 6B above. For the 3:1 ratio above, 1414 μg are weighed for a 10,000 IU hCG-IS ampoule, and 707 μg are weighed for 5000 IU hCG-IS ampoule, for example.

In use the material in ampoules is dissolved in 0.9% sterile saline using 1 cc of saline for each 1000 IU in the ampoule. The proper amount of preparation can be withdrawn from the ampoule with a syringe for injection, for example, intramuscularly or intravenously.

Those skilled in the art will appreciate from the above that the hormone preparations of this invention, i.e., hybrids of hCG-subunits, represent a hormone that is distinct from commercially available hCG preparations obtained by extraction procedures of native hCG from the urine of pregnant women.

The difference between commercial hCG and hCG hybrid preparations of this invention include the following: Commercial hCG apparently is a mixture of whole or intact hCG molecules and subunits where the ratio of α to β is substantially less than one, whereas the hybrid hormone preparations of this invention contain ratios of α to β subunits greater than one. The biological activity of the hybrid hormone preparations of this invention can be 6 or more times greater than that of commercial hCG. The biological effect at the ovarian level of the hybrid hormone preparations of the invention is more rapid than that of commercial hCG, which is probably due to a lower circulatory half-life of the hybrid hormone preparations than that of commercial hCG.

This invention has been described in detail with specific reference to the preferred embodiment thereof. However, it will be appreciated that those skilled in the art, upon reading this disclosure, may effect modifications within the spirit and scope of my invention.

I claim:

1. A lyophilized hormone preparation comprising a hybridized or recombined product of admixture of α-chorionic gonadotropin subunits and β-chorionic gonadotropin subunits, wherein the ratio of α subunits to β subunits is from about 2:1 to about 8:1, said product being present in an amount sufficient to provide the activity equivalent to at least 1 IU hCG-IS.

2. A lyophilized hybrid hormone composition comprising the preparation of claim 1.

3. The hormone preparation of claim 1 wherein the ratio of α subunits to β subunits is about 3:1.

4. The hormone preparation of claim 1 wherein the ratio of α subunits to β subunits is from about 2.5:1 to about 5:1.

5. The hormone preparation of claim 1 wherein each of said α subunits and said β subunits contain less than 5 wt percent native chorionic gonadotropin as an impurity.

6. A frozen hybrid hormone composition comprising the preparation of claim 1.

7. The hormone preparation of claim 1, wherein the α-chorionic gonadotropin subunits and β-chorionic gonadotropin subunits are human chorionic gonadotropin subunits.

8. A lyophilized hybrid hormone composition comprising the preparation of claim 7.

9. The hormone preparation of claim 7 wherein the ratio of α subunits to β subunits is about 3:1.

10. The hormone preparation of claim 7 wherein the ratio of α subunits to β subunits is from about 2.5:1 to about 5:1.

11. The hormone preparation of claim 7 wherein each of said α subunits and said β subunits contain less than 5 wt percent native chorionic gonadotropin as an impurity.

12. A frozen hybrid hormone preparation having the composition of claim 7.

13. An ampoule of a hybrid hormone preparation as claimed in any one of claims 1, 3, 4, 5, 7, 9, 10, or 11 having an activity equivalent to about 10,000 IU hCG-IS.

14. An ampoule of a hybrid hormone preparation as claimed in any one of claims 1, 3, 4, 5, 7, 9, 10 or 11 having an activity equivalent to about 5,000 IU hCG-IS.

15. A frozen hormone preparation having chorionic gonadotropin activity prepared by hybridizing α-chorionic gonadotropin subunits and β-chorionic gonadotropin subunits, the ratio of α subunits to β subunits being from about 2:1 to about 8:1, in amounts such that the hybridized product provides the activity equivalent to at least 1 IU hCG-IS, and freezing the hybridized product.

16. A lyophilized composition comprising the preparation of claim 15.

17. The hormone preparation of claim 15 wherein the ratio of α subunits to β subunits is about 3:1.

18. The hormone preparation of claim 15 wherein the ratio of α subunits to β subunits is from about 2.5:1 to about 5:1.

19. The hormone preparation of claim 15 wherein each of said α subunits and said β subunits contain less than 5 wt percent native chroionic gonadotropin as an impurity.

20. A frozen hybrid hormone preparation having the composition of claim 15.

21. A hormone preparation in accord with any one of claims 15, 17, 18 or 19 wherein said α-chorionic gonadotropin subunit and said β-chorionic gonadotropin subunits is of human origin.

22. A method for stimulating ovulation in mammals comprising administering a hormone preparation comprising a hybridized or recombined product of admixture of α-chorionic gonadotropin subunits and β-chorionic gonadotropin subunits wherein the ratio of α subunits to β subunits is from about 2:1 to about 8:1, said preparation having chroionic gonadotropin hormone activity equivalent to at least 1 international unit of international standard hCG.

23. The method of claim 22 wherein the ratio of α subunits to β subunits is greater than 1:1 and less than about 5:1.

24. The method of claim 22 wherein the ratio of α subunits to β subunits is about 3:1.

25. The method of claim 22 wherein each of said α subunits and said β subunits contain less than 5 wt percent native chorionic gonadotropin as an impurity.

26. The method of any one of claims 22, 24 or 25 wherein said α-chorionic gonadotropin subunit and said β-chorionic gonadotropin subunit is of human origin.

27. The method of any one of claims 22 or 24 through 26 wherein said hormone preparation contains an activity equivalent to 10,000 IU hCG-IS.

28. The method of any one of claims 22 or 24 through 26 wherein said hormone preparation contains an activity equivalent to 5,000 IU hCG-IS.

29. A pharmaceutical preparation comprising a hybridized or recombined product of admixture of α-chorionic gonadotropin subunits and β-chorionic gonadotropin subunits, the ratio of α subunits to β subunits being from about 2:1 to about 8:1, said product being present in an amount sufficient to provide the activity equivalent to at least 1 IU hCG-IS, and said product being in a pharmaceutically acceptable carrier.

30. The preparation of claim 29 wherein the ratio of α subunits to β subunits is about 3:1.

31. The preparation of claim 29 wherein the ratio of α subunits to β subunits is from about 2.5:1 to about 5:1.

32. The preparation of claim 29 wherein each of said α subunits and said β subunits contains less than 5 wt percent native chorionic gonadotropin as an impurity.

33. The preparation of claim 29 wherein said α and β subunits are α and β human gonadotropin subunits.

34. A method for stimulating ovulation in mammals comprising administering by injection the preparation of any of claims 29 or 30 wherein said pharmaceutically acceptable carrier is a liquid carrier.

35. A method of reducing the risks of multiple gestation in treating anovulatory infertility in female mammals, comprising administering a chorionic gonadotropin agent in an amount which is effective to stimulate ovulation, said chorionic gonadotropin agent comprising a hybridized or recombined product of admixture of α-chorionic gonadotropin subunits and β-chorionic gonadotropin subunits having a ratio of α subunits to β subunits of between about 2:1 and about 8:1.

36. The method of claim 35, further comprising administering effective amounts of luteinizing hormone and follicle stimulating hormone, prior to administering said chorionic gonadotropin agent.

37. The preparation of claim 29, 30, 31, 32 or 33 wherein the pharmaceutrically acceptable carrier comprises lactose.

* * * * *